(12) United States Patent
Lee et al.

(10) Patent No.: US 9,406,907 B2
(45) Date of Patent: Aug. 2, 2016

(54) ORGANIC LIGHT EMITTING DEVICE AND METHOD FOR MANUFACTURING THE SAME

(71) Applicant: LG DISPLAY CO., LTD., Seoul (KR)

(72) Inventors: Jaein Lee, Daejeon (KR); Mun Kyu Joo, Daejeon (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days.

(21) Appl. No.: 14/403,394

(22) PCT Filed: May 24, 2013

(86) PCT No.: PCT/KR2013/004580
§ 371 (c)(1),
(2) Date: Nov. 24, 2014

(87) PCT Pub. No.: WO2013/176521
PCT Pub. Date: Nov. 28, 2013

(65) Prior Publication Data
US 2015/0194633 A1    Jul. 9, 2015

(30) Foreign Application Priority Data

May 25, 2012   (KR) ........................ 10-2012-0056400

(51) Int. Cl.
*H01L 51/52*   (2006.01)
*C07D 487/14*   (2006.01)
(Continued)

(52) U.S. Cl.
CPC .......... *H01L 51/5265* (2013.01); *C07D 487/14* (2013.01); *H01L 51/5004* (2013.01); *H01L 51/506* (2013.01); *H01L 51/5206* (2013.01); *H01L 51/5221* (2013.01); *H01L 51/5271* (2013.01); *H01L 51/5275* (2013.01); *H01L 51/56* (2013.01); *H01L 51/0054* (2013.01); *H01L 51/0067* (2013.01); *H01L 51/0072* (2013.01); *H01L 2251/305* (2013.01); *H01L 2251/306* (2013.01); *H01L 2251/308* (2013.01); *H01L 2251/5307* (2013.01); *H01L 2251/558* (2013.01)

(58) Field of Classification Search
CPC ............ H01L 51/5265; H01L 51/5004; H01L 51/5221; H01L 51/56; H01L 51/5206; H01L 51/0054; H01L 51/0067
See application file for complete search history.

(56) References Cited

U.S. PATENT DOCUMENTS

2005/0140288 A1   6/2005  Suzuki
2006/0038484 A1*  2/2006  Noh et al. ..................... 313/499
(Continued)

FOREIGN PATENT DOCUMENTS

JP    2005197009       7/2005
JP    2007-012946 A    1/2007
(Continued)

*Primary Examiner* — Michele Fan
(74) *Attorney, Agent, or Firm* — Dentons US LLP

(57) ABSTRACT

The present application provides an organic light emitting device and a method for manufacturing the same, the organic light emitting device including a first electrode; an organic material layer; and a second electrode provided in consecutive order, the organic material layer further including a light emitting layer; and an optical length control layer provided between the light emitting layer and the second electrode, the optical length control layer including a first optical length control layer that includes a compound represented by the following Chemical Formula 1, the light produced in the light emitting layer being emitted through the first electrode.

26 Claims, 3 Drawing Sheets

(51) Int. Cl.
*H01L 51/50* (2006.01)
*H01L 51/56* (2006.01)
*H01L 51/00* (2006.01)

(56) References Cited

U.S. PATENT DOCUMENTS

| | | | |
|---|---|---|---|
| 2007/0001587 A1* | 1/2007 | Hatwar et al. | 313/504 |
| 2007/0001588 A1 | 1/2007 | Boroson et al. | |
| 2007/0009762 A1 | 1/2007 | Hamada et al. | |
| 2007/0024168 A1 | 2/2007 | Nishimura et al. | |
| 2007/0102698 A1* | 5/2007 | Kang et al. | 257/40 |
| 2007/0102737 A1 | 5/2007 | Kashiwabara et al. | |
| 2007/0221912 A1* | 9/2007 | Jeong et al. | 257/40 |
| 2008/0136318 A1 | 6/2008 | Kashiwabara | |
| 2008/0278072 A1* | 11/2008 | Noh et al. | 313/504 |
| 2008/0284324 A1 | 11/2008 | Chun et al. | |
| 2008/0284325 A1* | 11/2008 | Noh et al. | 313/504 |
| 2009/0009101 A1* | 1/2009 | Kang et al. | 315/250 |
| 2009/0079339 A1* | 3/2009 | Kang et al. | 313/504 |
| 2009/0184628 A1* | 7/2009 | Kang et al. | 313/504 |
| 2010/0320446 A1 | 12/2010 | Kang et al. | |
| 2010/0320481 A1* | 12/2010 | Kashiwabara | 257/88 |
| 2011/0043102 A1* | 2/2011 | Lee et al. | 313/504 |
| 2011/0049546 A1* | 3/2011 | Heikman et al. | 257/98 |
| 2011/0079774 A1* | 4/2011 | Kang et al. | 257/40 |
| 2011/0180792 A1* | 7/2011 | Lee et al. | 257/40 |
| 2012/0007071 A1* | 1/2012 | Joo et al. | 257/40 |
| 2012/0112172 A1* | 5/2012 | Kashiwabara | 257/40 |
| 2012/0199860 A1* | 8/2012 | Hodota | 257/98 |

FOREIGN PATENT DOCUMENTS

| | | |
|---|---|---|
| JP | 2007-302630 A | 11/2007 |
| JP | 2008-034288 A | 2/2008 |
| JP | 2008-084910 A | 4/2008 |
| JP | 2009-500794 A | 1/2009 |
| JP | 2011-008958 A | 1/2011 |
| KR | 1020060079225 | 7/2006 |
| KR | 1020070015085 | 2/2007 |
| KR | 100829761 | 5/2008 |
| KR | 1020080073256 | 8/2008 |

* cited by examiner

ORGANIC LIGHT EMITTING DEVICE AND METHOD FOR MANUFACTURING THE SAME

TECHNICAL FIELD

The present application relates to an organic light emitting device and method for manufacturing the same.

This application is a 35 USC §371 National Stage entry of International Application No. PCT/KR2013/004580, filed on May 24, 2013, which claims priority from and the benefits of Korean Patent Application No. 10-2012-0056400, filed with the Korean Intellectual Property Office on May 25, 2012, the entire contents of which are incorporated herein by reference.

BACKGROUND ART

An organic light emitting device (OLED) is typically formed of two electrodes (an anode and a cathode), with one or more organic material layers placed between these electrodes. In the organic light emitting device having such a structure, when a voltage is applied between the two electrodes, holes from the anode and electrons from the cathode flow into the organic material layer. The holes and the electrons are recombined to form excitons, and the excitons fall back to the ground state and emit photons that correspond to the energy difference. By this principle, the organic light emitting device generates visible light.

Recently, as the range of application of organic light emitting devices has broadened, studies on materials capable of improving the performance of organic light emitting devices have been actively conducted.

DISCLOSURE

Technical Problem

The present disclosure describes an organic light emitting device having a novel structure.

Technical Solution

One embodiment of the present application provides an organic light emitting device including a first electrode; a light emitting layer and a second electrode provided in consecutive order, the organic light emitting device further including an optical length control layer provided between the light emitting layer and the second electrode, the optical length control layer including a first optical length control layer that includes a compound represented by the following Chemical Formula 1, and the light produced in the light emitting layer being emitted through the first electrode.

[Chemical Formula 1]

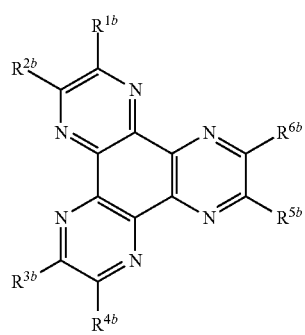

In the above Chemical Formula 1, each of $R^{1b}$ to $R^{6b}$ is selected from the group consisting of hydrogen, a halogen atom, nitrile (—CN), nitro (—NO$_2$), sulfonyl (—SO$_2$R), sulfoxide (—SOR), sulfonamide (—SO$_2$NR), sulfonate (—SO$_3$R), trifluoromethyl (—CF$_3$), ester (—COOR), amide (—CONHR or —CONRR'), substituted or unsubstituted linear or branched C$_1$-C$_{12}$ alkoxy, substituted or unsubstituted linear or branched C$_1$-C$_{12}$ alkyl, substituted or unsubstituted linear or branched C$_1$-C$_{12}$ alkenyl, a substituted or unsubstituted aromatic or nonaromatic heteroring, substituted or unsubstituted aryl, substituted or unsubstituted mono- or di-arylamine, and substituted or unsubstituted aralkylamine, and each of the above R and R' is selected from the group consisting of substituted or unsubstituted C$_1$-C$_{60}$ alkyl, substituted or unsubstituted aryl, and a substituted or unsubstituted 5 to 7-membered heteroring.

In the above description, "substituted or unsubstituted" means being unsubstituted or substituted with a halogen atom, nitrile (—CN), nitro (—NO$_2$), sulfonyl (—SO$_2$R), sulfoxide (—SOR), sulfonamide (—SO$_2$NR), sulfonate (—SO$_3$R), trifluoromethyl (—CF$_3$), ester (—COOR), amide (—CONHR or —CONRR'), linear or branched C$_1$-C$_{12}$ alkoxy, linear or branched C$_1$-C$_{12}$ alkyl, linear or branched C$_2$-C$_{12}$ alkenyl, an aromatic or nonaromatic heteroring, aryl, mono- or di-arylamine, or aralkylamine. Herein, each of the above R and R' is C$_2$-C$_{60}$ alkyl, aryl, or a 5 to 7-membered heteroring.

One embodiment of the present application provides an illumination device that includes the organic light emitting device.

One embodiment of the present application provides a method for manufacturing an organic light emitting device including the steps of forming a first electrode on a substrate; forming a light emitting layer on the first electrode; and forming a second electrode on the light emitting layer, the method further including the step of forming an optical length control layer between the light emitting layer and the second electrode, and the optical length control layer including a first optical length control layer that includes a compound represented by the above Chemical Formula 1.

Advantageous Effects

According to the present application, an organic light emitting device can be provided in which, by including an optical length control layer between a light emitting layer and an electrode placed at the opposite side of the surface that emits light, light emission efficiency can be improved without an increase in driving voltage since a cavity is controlled, and chromaticity is improved.

MODE FOR DISCLOSURE

Figure 1:
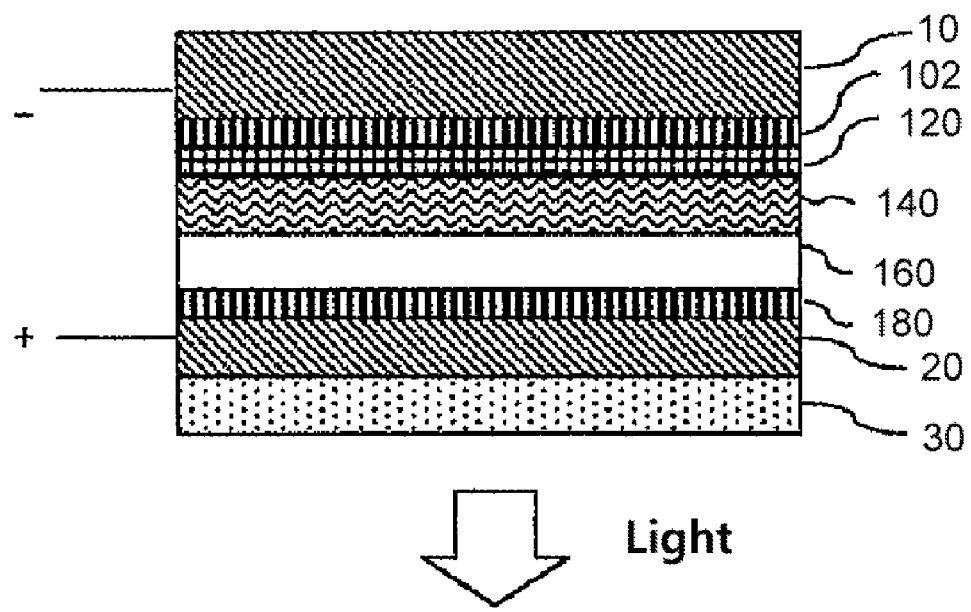
FIG. 1 to FIG. 3 illustrate the structure of an organic light emitting device according to one embodiment of the present application.

The advantages and features of the present application, and the methods to achieve these advantages and features will become clear when referencing the embodiments described below in detail with the attached drawings. However, the present application is not limited to the embodiments described below, and will be realized in various different forms, and the present embodiments make the delivery of the present application complete, and are provided in order to completely make known the range of the invention to those skilled in the art relating to the present application, and the present application is only defined by the scope of the claims. The size and the relative size of constitutions shown in the drawings may be exaggerated in order to clarify the description.

Unless otherwise specified, all the terms (including technical and scientific terms) used herein may be used according to the meanings commonly understandable to those skilled in the art relating to the present application. In addition, the terms defined in generally used dictionaries are not interpreted either ideally or immoderately unless clearly specially defined otherwise.

Hereinafter, the present application will be described in detail.

In an organic light emitting device that includes a substrate; a first electrode; a light emitting layer and a second electrode provided in consecutive order, the organic light emitting device according to one embodiment of the present application may include an optical length control layer provided between the light emitting layer and the second electrode. The optical length control layer may include a first optical length control layer that includes the compound represented by the above Chemical Formula 1. In addition, the optical length control layer may include a first optical length control layer that includes the compound represented by the above Chemical Formula 1, and a second optical length control layer that includes a transparent conductive material.

In the organic light emitting device according to one embodiment of the present application, the light produced in the light emitting layer emits light through the first electrode, and the second electrode means an electrode placed at the opposite side of the direction of light emission. Furthermore, by controlling the reflectivity of the electrode placed at the opposite side of the direction of light emission, both-sides light emission is also possible.

Meanwhile, in the organic light emitting device, a method of controlling the cavity of a device according to the color of light to be emitted may be used as one of the methods to increase light emission efficiency. Light emission efficiency can be further improved by controlling the cavity of a device to be suitable for the wavelength of the color of light emitted. In the present disclosure, the cavity of a device means the length in which light can resonate while traveling and/or going around within the device, and includes a light resonator that has a stationary wave between the two optical mirrors and forms a resonance, and/or all devices having such structures.

In addition, in the organic light emitting device, the distance between the light emitting layer and the second electrode can also have an influence on the light loss due to surface plasmon, a metal, a waveguide mode, a substrate mode, an out-coupled mode, or the like. Furthermore, light emission efficiency can be reduced when the distance from the light emitting layer to the second electrode is too small, since there are light emission absorption effects attributable to the dielectric constant of the second electrode itself. As a result, the distance from the light emitting layer to the second electrode may need to be adjusted.

When an electron transfer layer is included between the light emitting layer and the second electrode in order to alleviate the above phenomenon, the cavity length between the light emitting layer and the second electrode may be adjusted by adjusting the thickness of the electron transfer layer. However, this may cause a charge imbalance and have a voltage increasing effect. In the present disclosure, charge means an electron or a hole.

According to one embodiment of the present application, when the optical length control layer, which plays the role of a cavity control layer, is included between the light emitting layer and the second electrode, the voltage increasing effect can be prevented, and additionally the chromaticity of emitted light is excellent.

The compound represented by Chemical Formula 1 included in the first optical length control layer is crystalline, and thereby has excellent electrical conductivity, and has an advantage in that the voltage increasing effect is small even when the thickness of the organic material layer that includes this compound is increased.

The transparent conductive material included in the second optical length control layer may be one or more metal oxides selected from the group consisting of indium tin oxide (ITO), indium zinc oxide (IZO), indium oxide, tin oxide and zinc oxide (ZnO). The voltage increasing effect is also small when the thickness of the second optical length control layer that includes the transparent conductive material is increased.

For example, when the second electrode functions as a reflecting plate, the distance from the light emitting layer to the second electrode can be adjusted to a multiple of integers of [refractive index of organic material layer×$\lambda$/4] when the organic material layer is present between the light emitting layer and the second electrode. In this case, $\lambda$ is the wavelength of light emitted from the light emitting layer. Light of different colors has different wavelengths, therefore, the distance from the light emitting layer to the second electrode can be set differently depending on the color of the light emitted from the light emitting layer. In addition, when the refractive index of the organic material layer is changed, the length of a light path, represented by the multiplication of a refractive index and a thickness, also changes, therefore, the distance from the light emitting layer to the second electrode can be adjusted differently depending on the refractive index. The material of the second electrode can also have an influence on the distance from the light emitting layer to the second electrode. For example, in most metals, the length of the light path can vary depending on the penetration depth, that is, the distance to which the light penetrates deeper below the surface without being completely reflected on the surface. In silver (Ag), which has a penetration depth of 13 nm compared to aluminum (Al), which has a penetration depth of 7 nm, more light penetrates deeper inside the metal, so the distance from the light emitting layer to the second electrode is different.

When phase matching between the light that moves from the light emitting layer to the second electrode and the light that is reflected from the second electrode occurs, constructive interference occurs, and bright light can be obtained by the resultant amplification of the intensity of the emitted light. In contrast, when phase mismatching between the above lights occurs, destructive interference occurs, and as a result, some of the light is cancelled out. According to these phenomena of phase matching and phase mismatching, the brightness of the light emitted comes in the form of a sine curve depending on the distance from the light emitting layer to the second electrode.

According to one embodiment of the present application, in a sine curve showing the brightness of the light emitted from a device, which depends on the distance from the light emitting layer to the second electrode, the x axis value of the area in which the brightness of light is maximized may be set as the distance from the light emitting layer to the second electrode.

According to one embodiment of the present application, the thickness of the optical length control layer may be 50 Å or more, particularly greater than or equal to 50 Å and less than or equal to 10,000 Å, and more particularly greater than or equal to 200 Å and less than or equal to 3,000 Å, greater than or equal to 200 Å and less than or equal to 1,200 Å, greater than or equal to 200 Å and less than or equal to 1,000 Å, greater than or equal to 1,500 Å and less than or equal to 3,000 Å, greater than or equal to 1,500 Å and less than or equal to 2,500 Å, or greater than or equal to 1,700 Å and less than or equal to 3,000 Å.

The thickness of the optical length control layer can vary slightly depending on the wavelength of the color of emitted light. For example, for a blue device, in which the light to be produced in the light emitting layer is blue light, the thickness may be greater than or equal to 200 Å and less than or equal to 1,000 Å, or greater than or equal to 1,300 Å and less than or equal to 2,500 Å, and for a yellow device, in which the light to be produced in the light emitting layer is yellow light, the thickness may be greater than or equal to 200 Å and less than or equal to 1,200 Å, or greater than or equal to 1,500 Å and less than or equal to 3,000 Å. The thickness of the optical length control layer can vary depending on the thickness of the electron transfer layer. When the thickness of the optical length control layer is less than 50 Å, efficiency can be reduced by the loss of light attributable to surface plasmons, the light absorption of a metal, a waveguide mode, or the like. When the thickness of the optical length control layer is greater than 3,000 Å, there are no big differences in effectiveness. However, if the thickness of the optical length control layer is too large, the process is not economical, therefore, the thickness is preferably 10,000 Å or less.

The compound represented by the above Chemical Formula 1 may be a compound represented by any one of the following Chemical Formulae 1-1 to 1-6. However, the compound is not limited thereto.

[Chemical Formula 1-1]

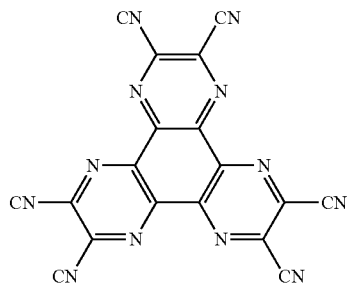

[Chemical Formula 1-2]

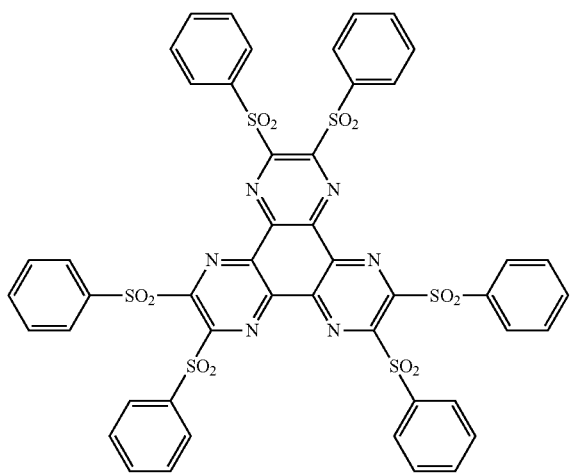

[Chemical Formula 1-3]

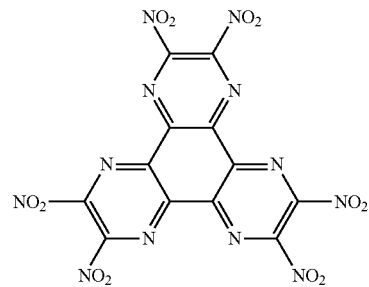

[Chemical Formula 1-4]

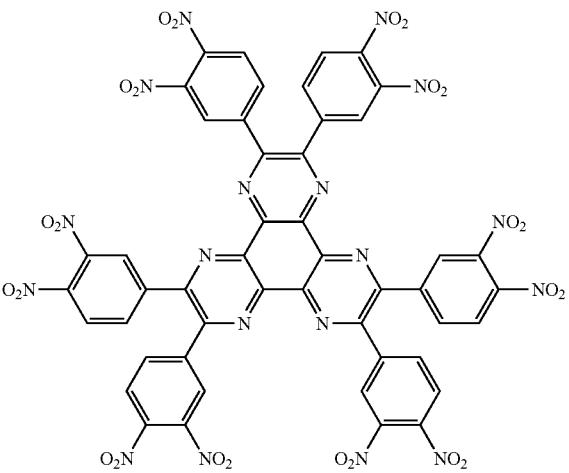

[Chemical Formula 1-5]

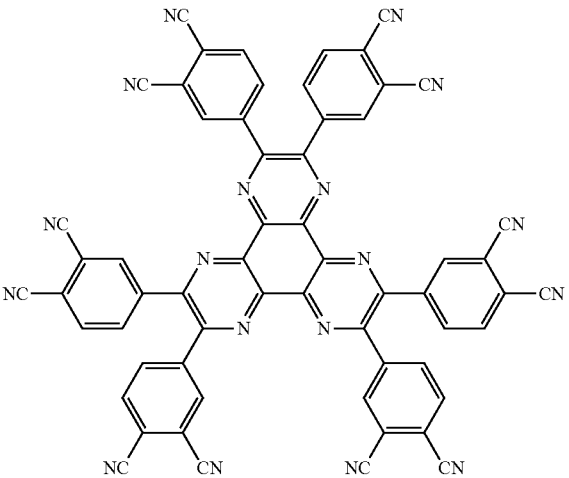

-continued

[Chemical Formula 1-6]

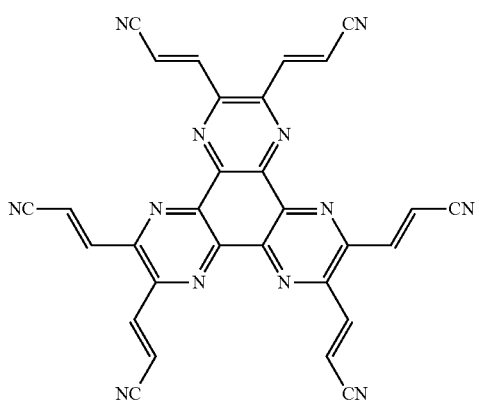

In one embodiment of the present application, a substrate that has a mechanical strength suitable for playing the role of a support may be included. The substrate may be included adjoined to the electrode from which light is emitted. Specifically, the substrate may be formed at the bottom of the first electrode.

As the substrate, a substrate having high transmittance or a substrate having high reflectivity may be selected, depending on the use. When a substrate having high reflectivity is needed, a substrate that has high reflectivity itself or a substrate coated with a material that has high reflectivity may be used. Examples of substrates used for this purpose include those made from plastic, glass, metal, ceramic, wafers, metal foil, and the like.

As the substrate used in conventional organic light emitting devices, a substrate such as glass, which can tolerate a high-temperature process condition, is used since ITO that is used as an anode is formed as a thin film using a sputtering process while the temperature of the substrate is maintained at a high temperature (>150° C.), and the ITO anode formed in this process condition is again plasma cleaned using oxygen or a mixed gas including oxygen, or is treated with ultraviolet light/ozone prior to the manufacturing of the organic light emitting device in order to increase the work function at the surface or remove contaminants present on the surface, the result of which is reduced driving voltage and improved reliability of the device. In the organic light emitting device of the present application, a conventional glass substrate may be used as it is, or various substrates having suitable mechanical strength and planarity may also be used.

The inventors have found that the optimal range in which high light emission efficiency and low driving voltage are exhibited is as described by the following Formula 1 and/or Formula 2, considering the refractive index of each organic material layer provided between the light emitting layer and the second electrode, which includes the optical length control layer, as well as the thickness of each organic material layer. Specifically, the inventors have found that, when the second electrode does not emit light and the reflectivity ranges from 70% to 100%, and the relationship between the thickness and the refractive index of the organic material layer provided between the light emitting layer and the second electrode satisfies the following Formula 1 and/or Formula 2, the organic light emitting device operates with high light emission efficiency and low driving voltage.

According to one embodiment of the present application, the organic light emitting device further includes m organic material layers between the light emitting layer and the second electrode, the m organic material layers satisfying the following Formula 1.

$$(\lambda/4 - 105) \leq \sum_{x=1}^{m} n_x d_x \leq (\lambda/4 - 20)$$ [Formula 1]

In the above Formula 1, $\lambda$ means the light wavelength (nm) of the light emitting layer, $n_x$ means the refractive index of the xth organic material layer from the light emitting layer in the direction of the second electrode, and $d_x$ means the thickness of the xth organic material layer from the light emitting layer in the direction of the second electrode.

In addition, according to one embodiment of the present application, the organic light emitting device may further include m organic material layers between the light emitting layer and the second electrode, the m organic material layers satisfying the following Formula 2.

$$(\lambda/4 + 100) \leq \sum_{x=1}^{m} n_x d_x \leq (\lambda/4 + 200)$$ [Formula 2]

In the above Formula 2, $\lambda$ means the light wavelength (nm) of the light emitting layer, $n_x$ means the refractive index of the xth organic material layer from the light emitting layer in the direction of the second electrode, and $d_x$ means the thickness of the xth organic material layer from the light emitting layer in the direction of the second electrode.

The m organic material layers may include an optical length control layer provided between the light emitting layer and the second electrode. In addition, the m organic material layers may include a hole blocking layer. Furthermore, the m organic material layers may include an electron transfer layer. In addition, the m organic material layers may include an electron injection layer.

In one embodiment of the present application, one or more organic material layers may be included between the second electrode and the light emitting layer, and/or between the light emitting layer and the optical length control layer.

In one embodiment of the present application, the organic light emitting device may include one or more organic material layers between the first electrode and the second electrode.

In one embodiment of the present application, one or more organic material layers may be included between the first electrode and the light emitting layer.

In one embodiment of the present application, one or more organic material layers may be included between the second electrode and the light emitting layer, and/or between the light emitting layer and the optical length control layer.

In one embodiment of the present application, the organic material layer may be an electron transfer layer provided between the cathode and the light emitting layer adjoined to the light emitting layer. The electron transfer layer may be included between the second electrode and the light emitting layer adjoined to the light emitting layer when the second electrode is a cathode. The electron transfer layer may be included between the first electrode and the light emitting layer adjoined to the light emitting layer when the first electrode is a cathode.

In one embodiment of the present application, the organic material layer may be a hole transfer layer provided between the anode and the light emitting layer adjoined to the light emitting layer. The hole transfer layer may be included between the first electrode and the light emitting layer adjoined to the light emitting layer when the first electrode is an anode. The hole transfer layer may be included between the second electrode and the light emitting layer adjoined to the light emitting layer when the second electrode is an anode.

In one embodiment of the present application, the organic material layer may be a hole injection layer provided between the anode and the light emitting layer adjoined to the anode.

In one embodiment of the present application, both the first electrode and the second electrode may be also formed with materials having various work functions by the organic material layer adjoined to each of the first electrode and the second electrode. For example, both the first electrode and the second electrode may use a material having a work function ranging from 2 eV to 6 eV, particularly a material having a work function ranging from 2 eV to 4 eV. The electrode material may include a material selected from the group consisting of a metal, a metal oxide and a conductive polymer.

In one embodiment of the present application, the first electrode may be an anode, and the second electrode may be a cathode. In this case, the device may be a normal bottom type, in which light emission occurs in the anode direction. In this case, a substrate may be included adjoined to the first electrode at the bottom of the first electrode.

In one embodiment of the present application, the first electrode may be a cathode, and the second electrode may be an anode. In this case, the device may be an inverted bottom type, in which light emission occurs in the cathode direction. In this case, a substrate may be included adjoined to the second electrode at the bottom of the second electrode.

The organic light emitting device according to one embodiment of the present application is preferably a normal bottom type, rather than an inverted bottom type, in terms of light emission efficiency.

The first electrode may form a thin film using a metal or a metal oxide having a relatively large work function, and specifically, the first electrode may be formed using a transparent material having a large work function. When an anode having a large work function is used, the difference between the valance band of the material forming the hole transfer layer and the work function of the anode is reduced, therefore, smooth injection of the holes can be made at a low voltage. As a result, in selecting the materials included in the anode and the hole transfer layer, the band position between the two materials, the adhesiveness of the interface, or the stability has a large influence on the efficiency and the life of a device. For example, the first electrode may be formed using one or more types of transparent metal oxides selected from each of indium tin oxide (ITO), indium zinc oxide (IZO), indium oxide, tin oxide and zinc oxide (ZnO). The material of the first electrode also affects light emission efficiency. An appropriate current can be supplied to the organic light emitting device having a large area only when a material having small electrical resistance is selected.

The material of the first electrode may have transmittance ranging from 5% to 100%. Specifically, when the transmittance ranges from 50% to 100%, light emission efficiency can be increased due to the decreased light loss. The first electrode means an electrode placed in the direction in which the light produced in the light emitting layer is emitted.

The refractive index of the first electrode preferably ranges from 1.3 to 2.5 in order to have favorable light emission efficiency, and more particularly, when the refractive index ranges from 1.5 to 2.3, light emission efficiency is further improved, since a waveguide effect is reduced.

The thickness of the first electrode preferably ranges from 300 Å to 1,700 Å. The first electrode needs to have favorable transmittance, and the thinner the electrode, the more favorable the transmittance that is obtained. In addition, resistance needs to be small. The first electrode preferably ranges from 300 Å to 1,700 Å in order to fall within the optimal ranges of both resistance and transmittance. In this range, light emission efficiency can be raised without increasing the voltage.

In one embodiment of the present application, the first electrode may additionally include a thin film of a metal or an alloy thereof, or a metal oxide layer at the interface at which the organic material layer is adjoined to the first electrode. The organic material layer may be a hole injection layer, a hole transfer layer, or an electron transfer layer.

When the thin film of a metal or an alloy thereof, or a metal oxide layer such as the above, is additionally included, the mobility of charges and electrical conductivity can be raised, which is therefore effective in lowering the threshold voltage and the operating voltage of a device. In addition, when an organic light emitting device having a large area is manufactured, electrode resistance can be reduced when a metal oxide such as indium zinc oxide is used as the first electrode, which is therefore effective in obtaining more uniform light from the light emitting part of a device.

The material of the additional layer included in the first electrode specifically includes aluminum (Al), silver (Ag), zinc (Zn), niobium (Nb), zirconium (Zr), tin (Sn), tantalum (Ta), vanadium (V), mercury (Hg), gallium (Ga), indium (In), cadmium (Cd), boron (B), hafnium (Hf), lanthanum (La), titanium (Ti), calcium (Ca), magnesium (Mg) and alloys of a metal selected among these and Nd or Pd, and also includes metal oxides such as $Li_2O$, $Na_2O$, $Rb_2O$, $Cs_2O$, MgO and CaO, but the material is not limited thereto.

When the thin film of a metal or an alloy thereof, or the metal oxide layer such as the above is additionally included, the thickness may be adjusted in consideration of the transmittance and the electrical conductivity of the wavelength of a visible light area, and the thickness preferably ranges from 1 Å to 300 Å.

The material that forms the second electrode in one embodiment of the present application is preferably a material having a small work function and high reflectivity, the reason for selecting a material having a small work function being to ensure that electron injection to the conduction band of the material that forms the electron transfer layer is smooth.

Specifically, the second electrode may include one, two or more alloys selected from the group consisting of Al, Ag, Au, Ni, Pd, Ti, Mo, Mg, Ca, Zn, Te, Pt and Ir, and more particularly, Al or Ag, which has excellent reflectivity, may be used.

In one embodiment of the present application, it is advantageous that the thickness of the second electrode is 700 Å or more, since the reflectivity thereof becomes 70% to 100%, and more particularly, 90% to 100%. In addition, when the area of an organic light emitting device is large, for example, as large as 9 $cm^2$ or more, the thickness of the second electrode may become 2,000 Å or more, so that the whole surface of the organic material is covered. The second electrode means an electrode placed at the opposite side of the direction of light emission.

In the present disclosure, n-type means n-type semiconductor properties. In other words, an n-type organic material layer is an organic material having properties such that electrons are injected or transferred at the lowest unoccupied molecular orbital (LUMO) energy level, and is an organic material layer having material properties such that the mobility of electrons is greater than the mobility of holes. In contrast, p-type means p-type semiconductor properties. In other words, a p-type organic material layer is an organic material having properties such that holes are injected or transferred at the highest occupied molecular orbital (HOMO) energy level, and is an organic material layer having material properties such that the mobility of holes is greater than the mobility of electrons. In the present disclosure, 'an organic material layer that transfers charges at the HOMO energy level' and a p-type organic material layer may be used interchangeably. In addition, 'an organic material layer that transfers charges at the LUMO energy level' and an n-type organic material layer may be used interchangeably.

In the present disclosure, the energy level means the magnitude of energy. Therefore, even when the energy level is described as being in the (−) direction from the vacuum level, this is interpreted to mean that the energy level is the absolute value of the corresponding energy value. For example, the HOMO energy level means the distance from the vacuum level to the highest occupied molecular orbital. In addition, the LUMO energy level means the distance from the vacuum level to the lowest unoccupied molecular orbital.

In one embodiment of the present application, the organic material layer adjoined to the first electrode may be a hole injection layer, and a hole transfer layer may be formed adjoined to the hole injection layer. In this case, the hole transfer layer may be a p-type organic material layer.

In addition, when the light emitting layer is a p-type organic material layer, the hole transfer layer may be omitted. In this case, the light emitting layer may be formed adjoined to the hole injection layer.

Furthermore, when the hole transfer layer plays the role of both hole injection and hole transfer, the hole injection layer may be omitted. In this case, the organic material layer adjoined to the first electrode may be the hole transfer layer.

The organic material layer adjoined to the first electrode may include the compound of Chemical Formula 1. In addition, the p-type organic material layer may be the hole transfer layer or the light emitting layer. In this case, the compound of the above Chemical Formula 1 is an n-type organic material, therefore, an NP junction structure may be formed between the p-type organic material layer and the organic material layer adjoined to the first electrode. It is preferable that the energy level difference between the LUMO level of the organic material layer adjoined to the first electrode and the HOMO level of the p-type organic material layer be adjusted so as to be reduced. The energy difference between the LUMO energy level of the organic material layer adjoined to the first electrode and the HOMO energy level of the p-type organic material layer is preferably 1 eV or less, and more preferably approximately 0.5 eV or less. This energy difference is preferably greater than or equal to −1 eV and less than or equal to 1 eV in terms of material selection, and more preferably ranges from approximately 0.01 to 1 eV.

When the energy level is selected within the above value range, holes are readily injected to the HOMO energy level of the p-type organic material layer through the LUMO energy level of the organic material layer adjoined to the first electrode. When the energy difference between the HOMO energy level of the p-type organic material layer and the LUMO energy level of the organic material layer adjoined to the first electrode is greater than 1 eV, driving voltage for the hole injection increases since an NP junction between the p-type organic material layer and the organic material layer adjoined to the first electrode is not readily formed. In other words, in one embodiment of the present application, an NP junction needs to satisfy the energy relationship described above, as well as the n-type organic material layer and the p-type organic material layer being physically adjoined.

When an NP junction is formed, holes or electrons are readily formed by an external voltage or light source. In other words, due to an NP junction, holes within the p-type organic material layer and electrons within the organic material layer adjoined to the first electrode are readily formed. Holes or electrons are simultaneously generated at the NP junction, therefore, electrons are transferred in the direction of the first electrode through the organic material layer adjoined to the first electrode, and holes are transferred in the direction of the p-type organic material layer. As a result, holes or electrons are readily formed within the energy difference range, and an increase in the driving voltage of a device can be reduced since the concentration of charges increases. The p-type organic material layer may be a hole transfer layer or a p-type light emitting layer.

When the p-type organic material layer is a hole transfer layer, the p-type organic material layer can be placed between the light emitting layer and the organic material layer adjoined to the first electrode. Herein, the highest occupied molecular orbital (HOMO) energy level of the hole transfer layer is preferably 5 eV or more, and more preferably greater than or equal to 5 eV and less than or equal to 6 eV. When the HOMO energy level is 5 eV or more, effective charge generation with the hole injection layer can be realized.

The hole injection layer may be formed adjoined to the first electrode. The hole injection material that is used to form the hole injection layer is preferably a material that can receive holes by injection from the anode at a low voltage, and the highest occupied molecular orbital (HOMO) of the hole injection material is preferably between the work function of an anode material and the HOMO of a circumjacent organic material layer. Specific examples of the hole injection material include metal porphyrin, oligothiophene, an arylamine-based organic material, hexanitrile hexaazatriphenylene, a quinacridone-based organic material, a perylene-based organic material, anthraquinone, polyaniline- and polythiophene-based conductive polymer, or the like, but the material is not limited thereto. Preferably, the hole injection material may include the compound of Chemical Formula 1. In addition, by using a metal oxide-doped hole injection material, beneficial properties, specifically, properties such as decreased energy level, decreased leakage current, and the prevention of a voltage increase can be exhibited.

The hole transfer layer may be formed adjoined to the light emitting layer. Specifically, in a normal structure, the hole transfer layer may be formed between the first electrode and the light emitting layer. In addition, when the hole injection layer is formed adjoined to the first electrode, the hole transfer layer may be formed between the hole injection layer and the light emitting layer. Furthermore, in an inverted structure, the hole transfer layer may be formed between the light emitting layer and the optical length control layer.

A suitable hole transfer material for forming the hole transfer layer is a material that has high mobility for holes, that is, a material that can receive holes from the anode or the hole injection layer and move the holes to the light emitting layer. Specific examples include an arylamine-based organic material, a conductive polymer, and a block copolymer having a conjugated part and an unconjugated part together, but the hole transfer material is not limited thereto.

The light emitting layer may be formed between the hole transfer layer and the electron transfer layer. The light emitting layer may be formed with a material that has favorable quantum efficiency for fluorescence and phosphorescence, that is, a material that can emit light in the visible region by bonding the holes and the electrons transferred from the hole transfer layer and the electron transfer layer, respectively. Specific examples include an 8-hydroxy-quinoline aluminum complex (Alq$_3$); carbazole-based compounds; dimerized styryl compounds; BAlq; 10-hydroxybenzo quinolone-metal compounds; benzoxazole-, benzothiazole- and benzimidazole-based compounds; poly(p-phenylenevinylene) (PPV)-based polymers; spiro compounds; polyfluorene; rubrene, and the like, but the material is not limited thereto.

The electron transfer layer may be formed adjoined to the light emitting layer. Specifically, in a normal structure, the electron transfer layer may be formed between the light emitting layer and the optical length control layer. In an inverted structure, the electron transfer layer may be formed between the first electrode and the light emitting layer. The electron transfer layer may be n-type doped, or may not be n-type doped. The electron transfer layer including an n-type dopant is effective in increasing the concentration of a carrier.

The electron transfer layer including an n-type dopant preferably has a thickness ranging from 0.5 Å to 50 Å. When the thickness of the electron transfer layer including an n-type dopant is greater than 50 Å, light emission efficiency can be reduced due to the absorption of visible light, and when the thickness is less than 0.5 Å, effective electron injection may be difficult since the uniformity of a thin film can decrease.

The n-type dopant in the electron transfer layer including an n-type dopant may be an organic material or an inorganic material. When the n-type dopant is an inorganic material, an alkali metal such as Li, Na, K, Rb, Cs or Fr; an alkali-earth metal such as Be, Mg, Ca, Sr, Ba or Ra; a metal halide such as LiF, KF, NaF, CSF, MGF$_2$ or CaF$_2$; a metal oxide such as MgO, CaO, BaO, SrO, Li$_2$O, Na$_2$O, K$_2$O or Cs$_2$O; a rare-earth metal such as La, Ce, Pr, Nd, Sm, Eu, Tb, Th, Dy, Ho, Er, Em, Gd, Yb, Lu, Y or Mn; or a metal compound including one or more metals selected from the above metals, such as an alkali metal compound or an alkali-earth metal compound may be included. Furthermore, the n-type dopant may also be a material including cyclopentadiene, cycloheptatriene, a 6-membered heteroring, or a condensed ring including these rings.

Herein, the n-type dopant may be present in an amount ranging from 1% by weight to 50% by weight based on the total weight of the material of an organic material layer including the n-type dopant. When the n-type dopant is used in the above % by weight range, there are advantages in that the absorption of light can be minimized while effective electron injection can be readily performed. In one embodiment of the present application, as the method of doping the n-type dopant, methods known in the related art may be used, and the scope of the present application is not limited to a particular method.

As the material doped to the electron transfer layer including an n-type dopant, that is, a host material, an electron injection or transfer material may be used. Examples of the host material include compounds having a functional group selected from an imidazole group, an oxazole group, a thiazole group, a quinoline group and a phenanthroline group, but the host material is not limited thereto.

Specific examples of the compound having one or more functional groups selected from an imidazole group, an oxazole group, a thiazole group, a quinoline group and a phenanthroline group include the compound of the following Chemical Formula 2 or 3:

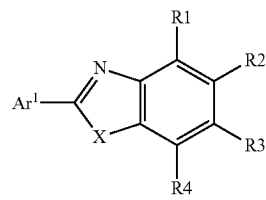

[Chemical Formula 2]

In the above Chemical Formula 2, R1 to R4 may be the same as or different from each other, and are each independently a hydrogen atom; a $C_1$-$C_{30}$ alkyl group unsubstituted or substituted with one or more groups selected from the group consisting of a halogen atom, an amino group, a nitrile group, a nitro group, a $C_1$-$C_{10}$ alkyl group, a $C_2$-$C_{30}$ alkenyl group, a $C_1$-$C_{30}$ alkoxy group, a $C_3$-$C_{30}$ cycloalkyl group, a $C_3$-$C_{30}$ heterocycloalkyl group, a $C_5$-$C_{30}$ aryl group and a $C_2$-$C_{30}$ heteroaryl group; a $C_3$-$C_{30}$ cycloalkyl group unsubstituted or substituted with one or more groups selected from the group consisting of a halogen atom, an amino group, a nitrile group, a nitro group, a $C_1$-$C_{30}$ alkyl group, a $C_2$-$C_{30}$ alkenyl group, a $C_1$-$C_{30}$ alkoxy group, a $C_3$-$C_{30}$ cycloalkyl group, a $C_3$-$C_{30}$ heterocycloalkyl group, a $C_5$-$C_{30}$ aryl group and a $C_2$-$C_{30}$ heteroaryl group; a $C_5$-$C_{30}$ aryl group unsubstituted or substituted with one or more groups selected from the group consisting of a halogen atom, an amino group, a nitrile group, a nitro group, a $C_1$-$C_{30}$ alkyl group, a $C_2$-$C_{30}$ alkenyl group, a $C_1$-$C_{30}$ alkoxy group, a $C_3$-$C_{30}$ cycloalkyl group, a $C_3$-$C_{30}$ heterocycloalkyl group, a $C_5$-$C_{30}$ aryl group and a $C_2$-$C_{30}$ heteroaryl group; or a $C_2$-$C_{30}$ heteroaryl group unsubstituted or substituted with one or more groups selected from the group consisting of a halogen atom, an amino group, a nitrile group, a nitro group, a $C_1$-$C_{30}$ alkyl group, a $C_2$-$C_{30}$ alkenyl group, a $C_1$-$C_{30}$ alkoxy group, a $C_3$-$C_{30}$ cycloalkyl group, a $C_3$-$C_{30}$ heterocycloalkyl group, a $C_5$-$C_{30}$ aryl group and a $C_2$-$C_{30}$ heteroaryl group, and, with an adjacent group, may form an aliphatic, aromatic, aliphatic hetero or aromatic hetero condensed ring, or may form a spiro bond; Ar$^1$ is a hydrogen atom, a substituted or unsubstituted aromatic ring, or a substituted or unsubstituted aromatic heteroring; X is O, S or NR$^a$; and R$^a$ is hydrogen, $C_1$-$C_7$ aliphatic hydrocarbon, an aromatic ring or an aromatic heteroring:

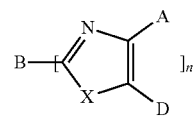

[Chemical Formula 3]

In the above Chemical Formula 3, X is O, S, NR$^b$ or a $C_1$-$C_7$ divalent hydrocarbon group; A, D and R$^b$ are each independently a hydrogen atom, a nitrile group (—CN), a nitro group (—NO$_2$), $C_1$-$C_{24}$ alkyl, a $C_5$-$C_{20}$ aromatic ring or a substituted aromatic ring including a hetero atom, halogen, alkylene capable of forming a fused ring with an adjacent ring or alkylene including a heteroatom; A and D are linked to form an aromatic or a hetero aromatic ring; B is a linking unit when n is 2 or more, is substituted or unsubstituted alkylene or arylene linking a plurality of heterorings to be conjugated or unconjugated, and is substituted or unsubstituted alkyl or aryl when n is 1; and n is an integer of 1 to 8.

Examples of the compound of the above Chemical Formula 2 include compounds disclosed in Korean Patent Application Laid-Open Publication No. 2003-0067773, and examples of the compound of the above Chemical Formula 3 include compounds disclosed in U.S. Pat. No. 5,645,948 and compounds disclosed in WO05/097756. The entire contents of the above documents are incorporated in the present disclosure by reference.

Specifically, the compound of the above Chemical Formula 2 includes the compound of the following Chemical Formula 4:

[Chemical Formula 4]

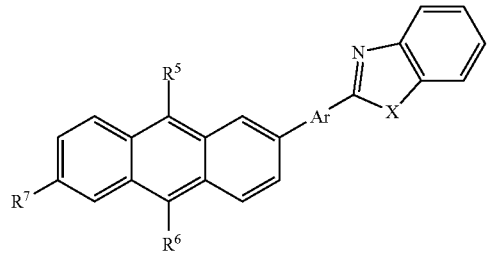

In the above Chemical Formula 4, $R^5$ to $R^7$ may be the same as or different from each other, are each independently a hydrogen atom, $C_1$-$C_{20}$ aliphatic hydrocarbon, an aromatic ring, an aromatic heteroring, or an aliphatic or an aromatic condensed ring; Ar is directly bonded, and is an aromatic ring or an aromatic heteroring; X is O, S or $NR^a$; and $R^a$ is a hydrogen atom, $C_1$-$C_7$ aliphatic hydrocarbon, an aromatic ring or an aromatic heteroring; however, the case in which both $R^5$ and $R^6$ are hydrogen is excluded.

In addition, the compound of the above Chemical Formula 3 includes the compound of the following Chemical Formula 5:

[Chemical Formula 5]

$$B \left[ \begin{array}{c} N \\ Z \end{array} \right]_n R^8$$

In the above Chemical Formula 5, Z is O, S or $NR^b$; $R^8$ and $R^b$ are a hydrogen atom, $C_1$-$C_{24}$ alkyl, a $C_5$-$C_{20}$ aromatic ring or a substituted aromatic ring including a heteroatom, halogen, alkylene capable of forming a fused ring with a benzazole ring or alkylene including a heteroatom; B is a linking unit when n is 2 or more, is alkylene, arylene, substituted alkylene, or substituted arylene linking a plurality of benzazoles to be conjugated or unconjugated, and is substituted or unsubstituted alkyl or aryl when n is 1; and n is an integer of 1 to 8.

The compound having an imidazole group as a preferable compound includes the compounds having the following structures:

-continued
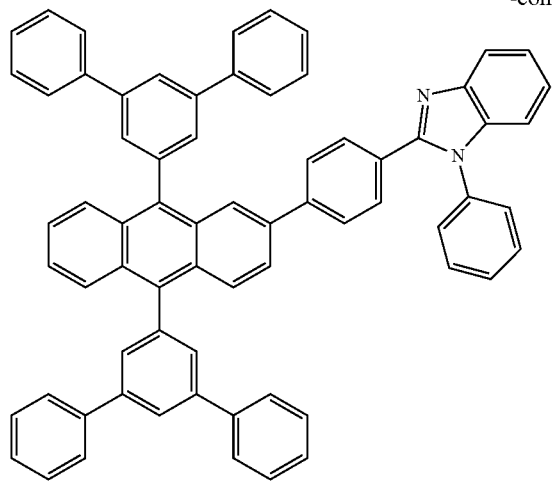
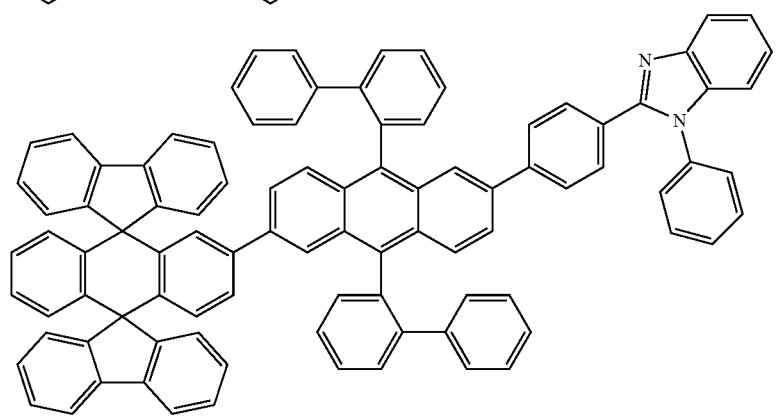
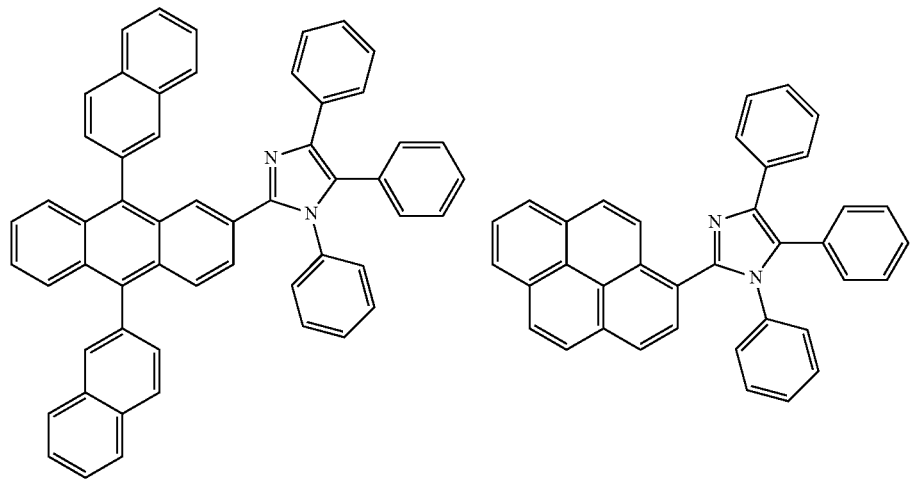
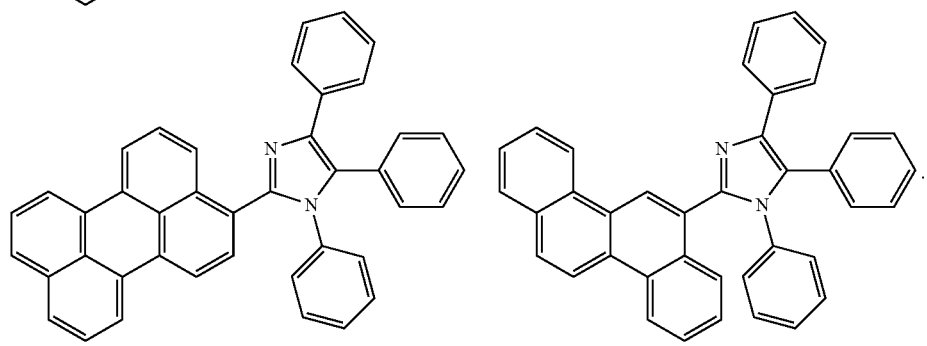

The organic material layer including an n-type dopant may improve the electron injection properties by lowering the energy barrier with the organic material layer adjoined to the second electrode due to the n-type doping. The difference between the LUMO level of the electron transfer layer including an n-type dopant and the LUMO level of the organic material layer adjoined to the second electrode is preferably 4 eV or less, and more preferably ranges from 2 eV to 3 eV. When an organic material layer having a LUMO level difference of greater than 4 eV is used, the electron injection properties may be reduced since the energy barrier with the organic material layer adjoined to the second electrode increases. When effective electron injection is not facilitated, it may result in an increase in the driving voltage. The organic material layer adjoined to the second electrode may be an optical length control layer.

A metal oxide layer or a metal salt layer may be additionally included between the electron transfer layer including an n-type dopant and the optical length control layer adjoined to the second electrode.

In the process of electron injection from the optical length control layer adjoined to the second electrode to the electron transfer layer including an n-type dopant, the metal oxide layer or the metal salt layer as the above may play the role of effectively preventing the transfer of holes from the HOMO energy level of the electron transfer layer including an n-type dopant to the optical length control layer adjoined to the second electrode. As a result, the effect of increasing the efficiency of a device can be expected by minimizing the annihilation phenomenon between the electrons and the holes and facilitating electron injection to the electron transfer layer including an n-type dopant. Specific examples of the metal oxide include $Li_2O$, $Na_2O$, $Rb_2O$, $Cs_2O$, MgO, CaO, and the like, and specific examples of the metal salt include LiF, NaF, KF, RbF, CsF, $MgF_2$, $CaF_2$, $SrF_2$, $BaF_2$, LiCl, NaCl, KCl, $RbCl$, CsCl, $MgCl_2$, $CaCl_2$, $SrCl_2$, $BaCl_2$, and the like, but the metal oxide and the metal salt are not limited thereto.

When the metal oxide or metal salt layer is included, the thickness thereof preferably ranges from 0.5 Å to 50 Å, and more preferably ranges from 1 Å to 20 Å. When the metal oxide or metal salt layer is too thick, it may cause an increase in the driving voltage of a device.

The organic material layer may be manufactured using a vapor deposition method, and may also be manufactured with less layers using a solution process such as spin coating, dip coating, doctor blading, screen printing, inkjet printing or a heat transfer method, using various polymer materials.

The examples of the materials that form each layer described above are only some of the examples provided to illuminate the present application, and the compounds the present application provides are not limited thereto.

Figure 2:
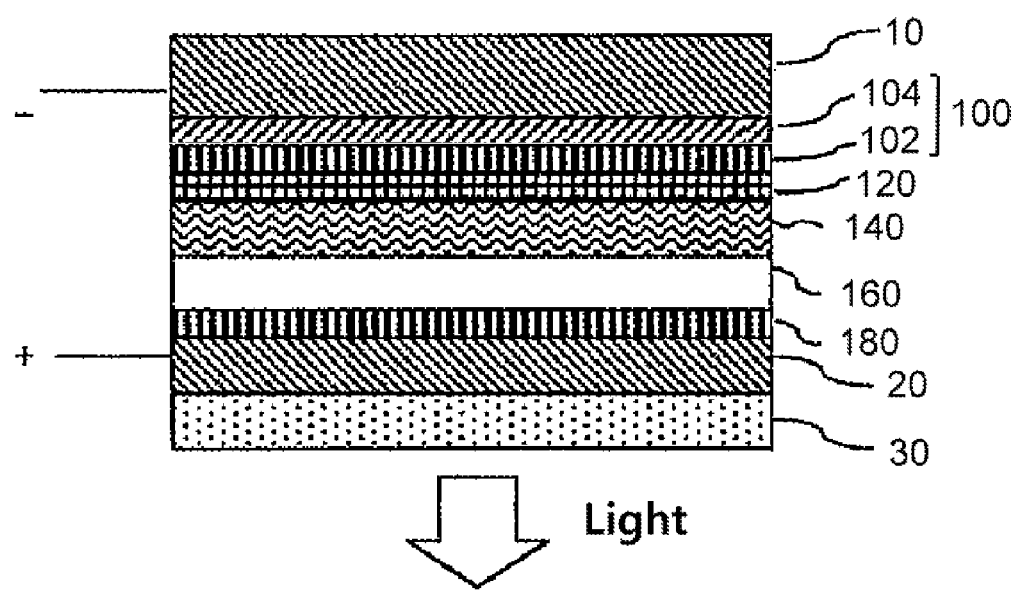
Figure 3:
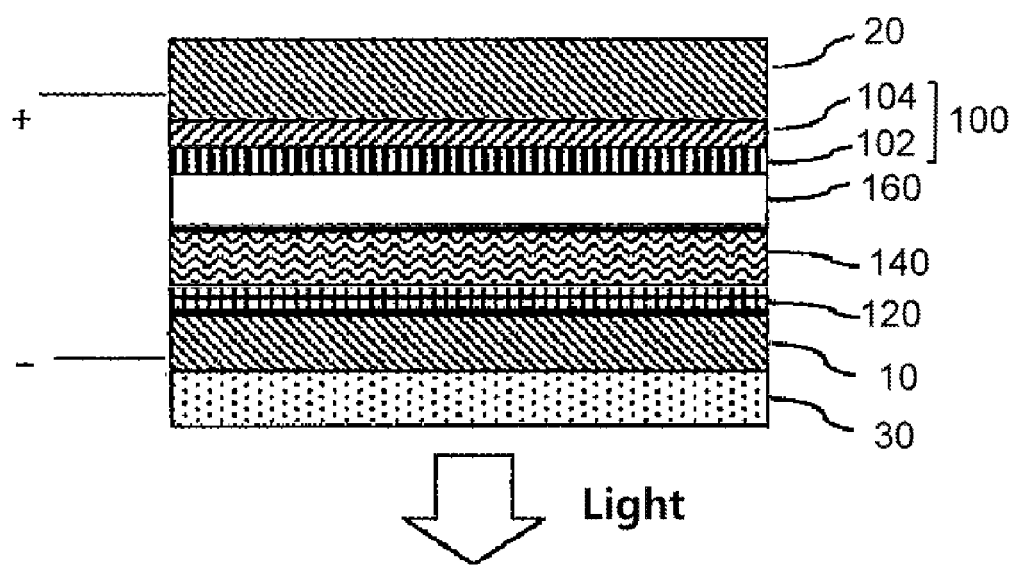

The organic light emitting device of the present application includes multiple organic layers between the anode and the cathode, and has a variety of structures using each layer described above. Basically, as a normal structure shown in FIG. 1, the organic light emitting device is manufactured including a substrate (30)/an anode (20)/a hole injection layer (180)/a hole transfer layer (160)/a light emitting layer (140)/ an electron transfer layer (120)/an optical length control layer (100)/and a cathode (10). In addition, the number of organic material layers may be reduced as necessary by using a material that can simultaneously play two or more roles as described in the description of each layer, or, on the contrary, the number of layers may be increased in order to further improve the performance or to exhibit special performance. As in FIG. 2, this layer structure may be a structure including a substrate (30)/an anode (20)/a hole injection layer (180)/a hole transfer layer (160)/a light emitting layer (140)/an electron transfer layer (120)/a first optical length control layer (102)/a second optical length control layer (104)/and a cathode (10), or a structure including a substrate/an anode/a hole transfer layer/a light emitting layer/an electron transfer layer/a first optical length control layer/a second optical length control layer/and a cathode. In addition, as an inverted structure shown in FIG. 3, the organic light emitting device may have a structure including a substrate (30)/a cathode (10)/an electron transfer layer (120)/a light emitting layer (140)/a hole transfer layer (160)/a first optical length control layer (102)/a second optical length control layer (104)/and an anode (20). However, the scope of the present application is not limited only to these structures.

An organic light emitting device according to one embodiment of the present application preferably has a normal structure in which a first electrode is a bottom electrode, as an anode, and a second electrode is a top electrode, as a cathode.

One embodiment of the present application provides an illumination device including the organic light emitting device.

One embodiment of the present application provides a method for manufacturing an organic light emitting device including the steps of forming a first electrode on a substrate; forming a light emitting layer on the first electrode; and forming a second electrode on the light emitting layer, the method further including the step of forming an optical length control layer between the light emitting layer and the second electrode, and the optical length control layer including a first optical length control layer that includes the compound represented by the above Chemical Formula 1.

In one embodiment of the present application, the step of forming the optical length control layer may further include the step of forming a second optical length control layer, which includes a transparent conductive material, between the first optical length control layer and the second electrode.

In one embodiment of the present application, the step of forming a hole transfer layer; the light emitting layer; and an electron transfer layer on the first electrode in consecutive order may be included prior to the step of forming the optical length control layer.

In one embodiment of the present application, the step of forming a hole injection layer including the compound represented by the above Chemical Formula 1; a hole transfer layer; the light emitting layer; and an electron transfer layer on the first electrode in consecutive order may be included prior to the step of forming the optical length control layer.

In one embodiment of the present application, the step of forming an electron transfer layer; the light emitting layer; and a hole transfer layer on the first electrode in consecutive order may be included prior to the step of forming the optical length control layer.

Hereinafter, various embodiments and characteristics of the present application will be described in greater detail with reference to examples and comparative examples. It is to be understood, however, that the following examples are for illustrative purposes only, and are not intended to limit the scope of the present application.

Example 1

IZO was formed on a substrate as an anode having a thickness of 1,000 Å using a sputtering method, and a p-type hole injection layer having a thickness of 500 Å was formed by thermal vapor depositing the following m-MTDATA (4,4',4"-tris[3-methylphenyl(phenyl)amino]triphenylamine) on the anode. Subsequently, a p-type hole transfer layer having a thickness of 400 Å was formed by vapor depositing the following NPB on the p-type hole injection layer.

Subsequently, a light emitting layer having a thickness of 300 Å was formed on the p-type hole transfer layer by doping the following chemical formula Ir(ppy)$_3$ (tris(2-phenylpyridine)iridium(III)) in an amount of 10% by weight to the following CBP (4,4'-N,N'-dicarbazole-biphenyl). On the light emitting layer, a hole blocking layer having a thickness of 50 Å was formed using the following BCP (2,9-dimethyl-4,7-diphenyl-1,10-phenanthroline).

An electron transfer layer having a thickness of 150 Å was formed on the hole blocking layer with the following electron transfer material as a host, and by doping Ca in an amount of 10% by weight as a dopant.

An optical length control layer having a thickness of 300 Å was formed by vapor depositing the following HAT (a compound represented by the above Chemical Formula 1-1) on the electron transfer layer.

Furthermore, an organic light emitting device was manufactured by forming Al to a thickness of 2,000 Å as a cathode on the optical length control layer.

In the above process, the vapor deposition rate of the organic material was maintained at 0.5 to 1 Å/sec, and the degree of vacuum at the time of deposition was maintained at approximately $2 \times 10^{-7}$ to $2 \times 10^{-8}$ torr.

The driving voltage and the external quantum efficiency according to the above Example 1 are shown in the following Table 1. The external quantum efficiency may have the same meaning as light emission efficiency.

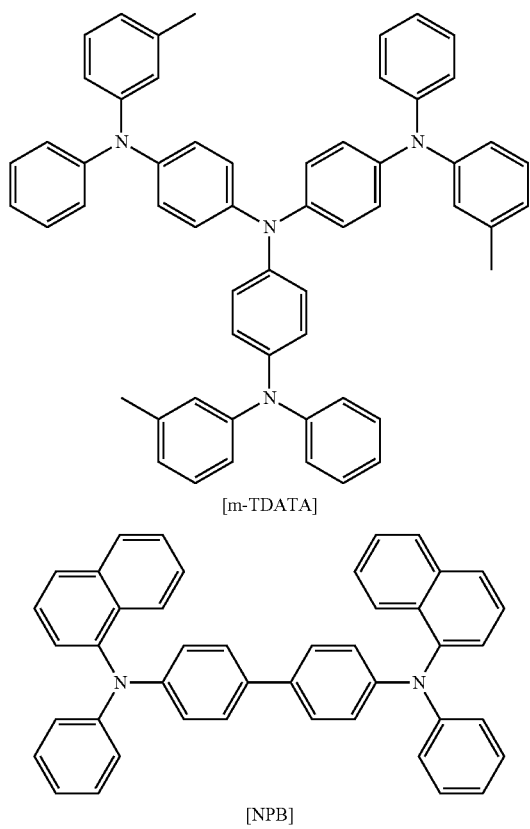

Example 2

An organic light emitting device was manufactured in the same manner as in Example 1, except that a first optical length control layer of 300 Å was formed on the electron transfer layer using the above HAT, a second optical length control layer having a thickness of 1,000 Å was formed by vapor depositing IZO on the first optical length control layer using a sputtering method, and Al was formed to a thickness of 2,000 Å as the cathode on the second optical length control layer.

The driving voltage and the external quantum efficiency according to the above Example 2 are shown in the following Table 1.

Example 3

An organic light emitting device was manufactured in the same manner as in Example 1, except that the anode was formed using IZO having a thickness of 500 Å, and the optical length control layer was formed to a thickness of 500 Å.

The driving voltage and the external quantum efficiency according to the above Example 3 are shown in the following Table 1.

Comparative Example 1

An organic light emitting device was manufactured in the same manner as in Example 1, except that the electron transfer layer having a thickness of 150 Å was formed on the hole blocking layer with the above electron transfer material as a host and by doping Ca in an amount of 10% by weight as a dopant, and Al was formed to a thickness of 2,000 Å as a cathode on the electron transfer layer. In other words, in Comparative Example 1, an organic light emitting device was manufactured as in Example 1 except that the optical length control layer was omitted.

The driving voltage and the external quantum efficiency according to the above Comparative Example 1 are shown in the following Table 1.

Comparative Example 2

An organic light emitting device was manufactured in the same manner as in Comparative Example 1, except that the electron transfer layer was formed to a thickness of 130 Å.

The driving voltage and the external quantum efficiency according to the above Comparative Example 2 are shown in the following Table 1.

Example 4

IZO was formed on a substrate as an anode having a thickness of 1,000 Å using a sputtering method, and a p-type hole injection layer having a thickness of 500 Å was formed by thermal vapor depositing the above HAT on the anode. Subsequently, a p-type hole transfer layer having a thickness of 300 Å was formed by vapor depositing the above NPB on the p-type hole injection layer.

Subsequently, a light emitting layer having a thickness of 200 Å was formed on the p-type hole transfer layer by doping the above chemical formula Ir(ppy)$_3$ (tris(2-phenylpyridine)iridium(III)) in an amount of 10% by weight to the above CBP (4,4'-N,N'-dicarbazole-biphenyl). On the light emitting layer, a hole blocking layer having a thickness of 50 Å was formed using the above BCP (2,9-dimethyl-4,7-diphenyl-1,10-phenanthroline).

An electron transfer layer having a thickness of 150 Å was formed on the hole blocking layer with the above electron transfer material as a host, and by doping Ca in an amount of 10% by weight as a dopant.

An optical length control layer having a thickness of 1,750 Å was formed by vapor depositing the above HAT (the compound represented by the above Chemical Formula 1-1) on the electron transfer layer.

Furthermore, an organic light emitting device was manufactured by forming Al to a thickness of 1,000 Å as a cathode on the optical length control layer.

In the above process, the vapor deposition rate of the organic material was maintained at 0.5 to 1 Å/sec, and the degree of vacuum at the time of deposition was maintained at approximately $2 \times 10^{-7}$ to $2 \times 10^{-8}$ torr.

The driving voltage and the external quantum efficiency according to the above Example 4 are shown in the following Table 2.

Example 5

An organic light emitting device was manufactured in the same manner as in Example 3, except that a blue light emitting layer was formed on the hole transfer layer by doping BAlq (bis(2-methyl-8-quinolinolate)-4-(phenylphenolato)aluminum) in an amount of 3% by weight to the above NPB, and the optical length control layer was formed to a thickness of 400 Å.

According to the above Example 5, it can be seen that, in an organic light emitting device that includes a blue light emitting layer, normal driving was also possible.

The driving voltage and the external quantum efficiency according to the above Example 5 are shown in the following Table 2.

TABLE 1

| | Thickness of Anode | Optical Length Control Layer | Thickness of Optical Length Control Layer | Driving Voltage (@5 mA/cm$^2$) | External Quantum Efficiency (@5 mA/cm$^2$) |
|---|---|---|---|---|---|
| Example 1 | 1,000 Å | HAT | 300 Å | 8.0 V | 15.4% |
| Example 2 | 1,000 Å | HAT/IZO | 300/1,000 Å | 5.2 V | 16.2% |
| Example 3 | 500 Å | HAT | 500 Å | 9.6 V | 11.6% |
| Comparative Example 1 | 1,000 Å | — | — | 13.7 V | 11.9% |
| Comparative Example 2 | 1,000 Å | — | — | 9.7 V | 5.4% |

Example 6

An organic light emitting device was manufactured in the same manner as in Example 3, except that a first optical length control layer of 300 Å was formed on the electron transfer layer using the above HAT, a second optical length control layer having a thickness of 1,600 Å was formed on the first optical length control layer using IZO, and Ag was formed to a thickness of 2,000 Å as the cathode on the second optical length control layer.

The driving voltage and the external quantum efficiency according to the above Example 6 are shown in the following Table 2.

TABLE 2

| | Light Emitting Layer | Optical Length Control Layer | Thickness of Optical Length Control Layer | Driving Voltage (@5 mA/cm$^2$) | External Quantum Efficiency (@5 mA/cm$^2$) |
|---|---|---|---|---|---|
| Example 4 | CBP: Ir(ppy)$_3$ | HAT | 1,750 Å | 8.2 V | 15.7% |
| Example 5 | NPB: BAlq | HAT | 400 Å | 5.2 V | 5.2% |
| Example 6 | CBP: Ir(ppy)$_3$ | HAT/IZO | 300/1,600 Å | 7.8 V | 14.8% |
| Comparative Example 1 | CBP: Ir(ppy)$_3$ | — | — | 13.7 V | 11.9% |

Comparative Example 3

IZO was formed on a substrate as an anode having a thickness of 1,000 Å using a sputtering method, and a p-type hole injection layer having a thickness of 500 Å was formed by thermal vapor depositing the above HAT on the anode. Subsequently, a p-type hole transfer layer having a thickness of 400 Å was formed by vapor depositing the above NPB on the p-type hole injection layer.

Subsequently, a light emitting layer having a thickness of 300 Å was formed on the p-type hole transfer layer by doping the above chemical formula Ir(ppy)$_3$ (tris(2-phenylpyridine)iridium(III)) in an amount of 10% by weight to the above CBP (4,4'-N,N'-dicarbazole-biphenyl). On the light emitting layer, a hole blocking layer having a thickness of 50 Å was formed using the above BCP (2,9-dimethyl-4,7-diphenyl-1,10-phenanthroline).

An electron transfer layer having a thickness of 150 Å was formed on the hole blocking layer with the above electron transfer material as a host, and by doping Ca in an amount of 10% by weight as a dopant.

An organic light emitting device was manufactured by forming Al to a thickness of 2,000 Å as a cathode on the electron transfer layer, and forming an optical length control layer to a thickness of 500 Å on the cathode using the above HAT.

In the above process, the vapor deposition rate of the organic material was maintained at 0.5 to 1 Å/sec, and the degree of vacuum at the time of deposition was maintained at approximately $2 \times 10^{-7}$ to $2 \times 10^{-8}$ torr.

The driving voltage and the external quantum efficiency according to the above Comparative Example 3 are shown in the following Table 3.

Comparative Example 4

An organic light emitting device was manufactured in the same manner as in Comparative Example 3, except that the optical length control layer was formed on the IZO anode by vapor depositing HAT to a thickness of 500 Å, and the optical length control layer was not formed on the cathode.

The driving voltage and the external quantum efficiency according to the above Comparative Example 4 are shown in the following Table 3.

TABLE 3

| | Location of Optical Length Control Layer | Optical Length Control Layer | Thickness of Optical Length Control Layer | Driving Voltage (@5 mA/cm$^2$) | External Quantum Efficiency (@5 mA/cm$^2$) |
|---|---|---|---|---|---|
| Example 1 | Between electron transfer layer and cathode | HAT | 300 Å | 8.0 V | 15.4% |
| Example 6 | Between electron transfer layer and cathode | HAT/IZO | 300/1,600 Å | 7.8 V | 14.8% |
| Comparative Example 3 | Above cathode | HAT | 500 Å | 13.7 V | 11.9% |
| Comparative Example 4 | Between anode and p-type hole injection layer | HAT | 500 Å | 12.9 V | 10.9% |

Comparative Example 5

An organic light emitting device was manufactured in the same manner as in Example 1, except that Al was formed to a thickness of 500 Å as the cathode, and the optical length control layer was formed to a thickness of 500 Å.

The driving voltage and the external quantum efficiency according to the above Comparative Example 5 are shown in the following Table 4.

TABLE 4

| | Optical Length Control Layer | Thickness of Cathode | Reflectivity of Cathode (@550 nm Wavelength) | Driving Voltage (@5 mA/cm²) | External Quantum Efficiency (@5 mA/cm²) |
|---|---|---|---|---|---|
| Example 1 | HAT 300 Å | Al 2,000 Å | 90% | 8.0 V | 15.4% |
| Comparative Example 5 | HAT 500 Å | Al 500 Å | 85% | 8.2 V | 13.2% |

Those skilled in the art relating to the present application will be able to perform various applications and modifications within the scope of the present application based on the above contents.

Hereinbefore, specific parts of the present application have been described, and it is obvious that, for those skilled in the art, these specific descriptions are only preferable embodiments, and do not limit the scope of the present application. Therefore, the actual scope of the present application is defined by the attached claims and equivalents thereof.

REFERENCES

10: Cathode
20: Anode
30: Substrate
100: Optical Length Control Layer
102: First Optical Length Control Layer
104: Second Optical Length Control Layer
120: Electron Transfer Layer
140: Light Emitting Layer
160: Hole Transfer Layer
180: Hole Injection Layer

The invention claimed is:

1. An organic light emitting device comprising a first electrode; a light emitting layer; and a second electrode provided in consecutive order, the organic light emitting device comprising:
   an optical length control layer provided between the light emitting layer and the second electrode, and
   m organic material layers between the light emitting layer and the second electrode, wherein the m organic material layers satisfy the following Formula 1 or Formula 2:

$$(\lambda/4 - 105) \leq \sum_{x=1}^{m} n_x d_x \leq (\lambda/4 - 20) \quad \text{[Formula 1]}$$

$$(\lambda/4 + 100) \leq \sum_{x=1}^{m} n_x d_x \leq (\lambda/4 + 200) \quad \text{[Formula 2]}$$

wherein, in the above Formula 1 and Formula 2, λ means a light wavelength (nm) of the light emitting layer, $n_x$ means a refractive index of an xth organic material layer from the light emitting layer in a direction of the second electrode, and $d_x$ means a thickness of an xth organic material layer from the light emitting layer in the direction of the second electrode,
   wherein the optical length control layer includes a first optical length control layer that includes a following compound represented by Chemical Formula 1;
   a light produced in the light emitting layer is emitted through the first electrode; and
   a thickness of the optical length control layer is greater than or equal to 200 Å and less than or equal to 3,000 Å:

[Chemical Formula 1]

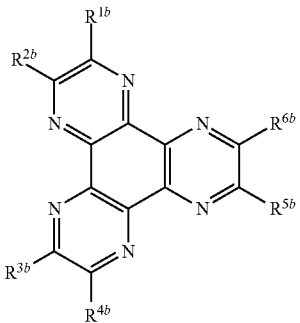

wherein, in the above Chemical Formula 1, each of $R^{1b}$ to $R^{6b}$ is selected from the group consisting of hydrogen, a halogen atom, nitrile (—CN), nitro (—NO₂), sulfonyl (—SO₂R), sulfoxide (—SOR), sulfonamide (—SO₂NR), sulfonate (—SO₃R), trifluoromethyl (—CF₃), ester (—COOR), amide (—CONHR or —CONRR'), substituted or unsubstituted linear or branched $C_1$-$C_{12}$ alkoxy, substituted or unsubstituted linear or branched $C_1$-$C_{12}$ alkyl, substituted or unsubstituted linear or branched $C_2$-$C_{12}$ alkenyl, a substituted or unsubstituted aromatic or nonaromatic heteroring, substituted or unsubstituted aryl, substituted or unsubstituted mono- or di-arylamine, and substituted or unsubstituted aralkylamine, and each of the above R and R' is selected from the group consisting of substituted or unsubstituted $C_1$-$C_{60}$ alkyl, substituted or unsubstituted aryl, and a substituted or unsubstituted 5 to 7-membered heteroring.

2. The organic light emitting device of claim 1, wherein, when the light produced in the light emitting layer is blue light, a thickness of the optical length control layer is greater than or equal to 200 Å and less than or equal to 1,000 Å, or greater than or equal to 1,300 Å and less than or equal to 2,500 Å.

3. The organic light emitting device of claim 1, wherein, when the light produced in the light emitting layer is yellow light, a thickness of the optical length control layer is greater than or equal to 200 Å and less than or equal to 1,200 Å, or greater than or equal to 1,500 Å and less than or equal to 3,000 Å.

4. The organic light emitting device of claim 1, wherein the optical length control layer further includes a second optical length control layer that includes a transparent conductive material.

5. The organic light emitting device of claim 4, wherein the transparent conductive material includes one or more metal oxides selected from the group consisting of indium tin oxide (ITO), indium zinc oxide (IZO), indium oxide, tin oxide and zinc oxide (ZnO).

6. The organic light emitting device of claim 1, wherein a transmittance of the first electrode ranges from 5% to 100%.

7. The organic light emitting device of claim 1, wherein a refractive index of the first electrode ranges from 1.3 to 2.5.

8. The organic light emitting device of claim 1, wherein the first electrode includes a material selected from the group consisting of a metal, a metal oxide and a conductive polymer, which have a work function ranging from 2 eV to 6 eV.

9. The organic light emitting device of claim 1, wherein a thickness of the first electrode ranges from 300 Å to 1,700 Å.

10. The organic light emitting device of claim 1, wherein a reflectivity of the second electrode ranges from 70% to 100%.

11. The organic light emitting device of claim 1, wherein the second electrode includes a material selected from the group consisting of a metal, a metal oxide and a conductive polymer, which have a work function ranging from 2 eV to 6 eV.

12. The organic light emitting device of claim 1, wherein a thickness of the second electrode is 700 Å or more.

13. The organic light emitting device of claim 1, further comprising:
an electron transfer layer provided adjoined to the light emitting layer,
wherein the electron transfer layer includes a compound having one or more functional groups selected from the group consisting of an imidazole group, an oxazole group, a thiazole group, a quinoline group and a phenanthroline group.

14. The organic light emitting device of claim 13, wherein the electron transfer layer includes an n-type dopant.

15. The organic light emitting device of claim 14, wherein a content of the n-type dopant ranges from 1 to 50% by weight.

16. The organic light emitting device of claim 14, wherein the electron transfer layer is provided between the light emitting layer and the optical length control layer, and an energy difference between the lowest unoccupied molecular orbital (LUMO) level of the electron transfer layer and the LUMO level of the optical length control layer is 4 eV or less.

17. The organic light emitting device of claim 1, further comprising:
a hole transfer layer provided adjoined to the light emitting layer.

18. The organic light emitting device of claim 17, wherein the hole transfer layer includes a p-type dopant.

19. The organic light emitting device of claim 18, wherein a highest occupied molecular orbital (HOMO) level of the hole transfer layer including the p-type dopant is 5 eV or more.

20. The organic light emitting device of claim 1, further comprising:
a hole transfer layer provided between the first electrode and the light emitting layer; and
a hole injection layer provided between the first electrode and the hole transfer layer,
wherein the hole injection layer includes the compound represented by Chemical Formula 1.

21. An illumination device including the organic light emitting device of claim 1.

22. A method for manufacturing an organic light emitting device comprising the steps of forming a first electrode on a substrate; forming a light emitting layer on the first electrode; and forming a second electrode on the light emitting layer, the method for manufacturing an organic light emitting device comprising the step of:
forming an optical length control layer between the light emitting layer and the second electrode; and
forming m organic material layers between the light emitting layer and the second electrode, wherein the m organic material layers satisfy the following Formula 1 or Formula 2:

$$(\lambda/4 - 105) \le \sum_{x=1}^{m} n_x d_x \le (\lambda/4 - 20) \quad \text{[Formula 1]}$$

$$(\lambda/4 + 100) \le \sum_{x=1}^{m} n_x d_x \le (\lambda/4 + 200) \quad \text{[Formula 2]}$$

wherein, in the above Formula 1 and Formula 2, $\lambda$ means a light wavelength (nm) of the light emitting layer, $n_x$ means a refractive index of an xth organic material layer from the light emitting layer in a direction of the second electrode, and $d_x$ means a thickness of an xth organic material layer from the light emitting layer in the direction of the second electrode,
wherein the optical length control layer includes a first optical length control layer including a compound represented by the following Chemical Formula 1; and
a light produced in the light emitting layer is emitted through the first electrode:

[Chemical Formula 1]

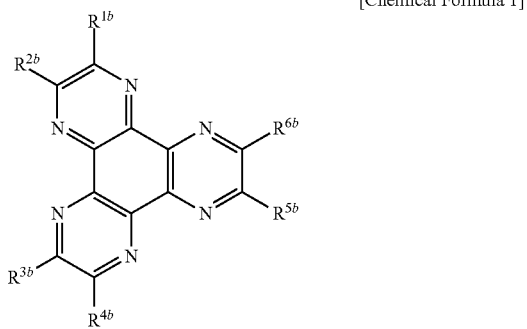

wherein, in the above Chemical Formula 1, each of $R^{1b}$ to $R^{6b}$ is selected from the group consisting of hydrogen, a halogen atom, nitrile (—CN), nitro (—NO$_2$), sulfonyl (—SO$_2$R), sulfoxide (—SOR), sulfonamide (—SO$_2$NR), sulfonate (—SO$_3$R), trifluoromethyl (—CF$_3$), ester (—COOR), amide (—CONHR or —CONRR'), substituted or unsubstituted linear or branched C$_1$-C$_{12}$ alkoxy, substituted or unsubstituted linear or branched C$_1$-C$_{12}$ alkyl, substituted or unsubstituted linear or branched C$_2$-C$_{12}$ alkenyl, a substituted or unsubstituted aromatic or nonaromatic heteroring, substituted or unsubstituted aryl, substituted or unsubstituted mono- or di-arylamine, and substituted or unsubstituted aralkylamine, and each of the above R and R' is selected from the group consisting of substituted or unsubstituted C$_1$-C$_{60}$ alkyl, substituted or unsubstituted aryl, and a substituted or unsubstituted 5 to 7-membered heteroring.

23. The method for manufacturing an organic light emitting device of claim 22, wherein the step of forming the optical length control layer further includes the step of forming a second optical length control layer, which includes a transparent conductive material, between the first optical length control layer and the second electrode.

24. The method for manufacturing an organic light emitting device of claim 22, wherein the step of forming a hole transfer layer; the light emitting layer; and an electron transfer layer on the first electrode in consecutive order is included prior to the step of forming the optical length control layer.

25. The method for manufacturing an organic light emitting device of claim 22, further comprising steps of forming a hole injection layer including the compound represented by the above Chemical Formula 1; a hole transfer layer; the light emitting layer; and an electron transfer layer on the first electrode in consecutive order prior to the step of forming the optical length control layer.

26. The method for manufacturing an organic light emitting device of claim 22, further comprising steps of forming an electron transfer layer; the light emitting layer; and a hole transfer layer on the first electrode in consecutive order prior to the step of forming the optical length control layer.

\* \* \* \* \*